US007713517B2

(12) United States Patent
Annapragada et al.

(10) Patent No.: US 7,713,517 B2
(45) Date of Patent: May 11, 2010

(54) COMPOSITIONS AND METHODS FOR ENHANCING CONTRAST IN IMAGING (75) Inventors: Ananth Annapragada, Manvel, TX (US); Ravi V. Bellamkonda, Marietta, GA (US); Eric Hoffman, Iowa City, IA (US); Chandra Vijayalakshmi, Manvel, TX (US)

(73) Assignee: Marval Biosciences, Inc., Houston, TX (US)

( * ) Notice: Subject to any disclaimer, the term of this patent is extended or adjusted under 35 U.S.C. 154(b) by 1323 days.

(21) Appl. No.: 10/830,190

(22) Filed: Apr. 21, 2004

(65) Prior Publication Data

US 2005/0238584 A1  Oct. 27, 2005

(51) Int. Cl.
*A61K 8/00* (2006.01)
*A61K 9/00* (2006.01)
*A61K 49/04* (2006.01)

(52) U.S. Cl. .................... 424/9.4; 424/9.41; 424/9.411; 424/9.42; 424/9.43; 424/9.44; 424/9.45; 424/9.451; 424/47

(58) Field of Classification Search ....... 424/9.4–9.451, 424/47
See application file for complete search history.

(56) References Cited

U.S. PATENT DOCUMENTS

| 4,744,989 | A | * | 5/1988 | Payne et al. ................. 424/490 |
| 5,049,389 | A | | 9/1991 | Radhakrishnan |
| 5,204,085 | A | * | 4/1993 | VanDeripe ................. 424/9.42 |
| 5,312,615 | A | | 5/1994 | Scheider et al. |
| 5,676,928 | A | * | 10/1997 | Klaveness et al. ......... 424/9.321 |
| 6,217,849 | B1 | * | 4/2001 | Tournier et al. .......... 424/9.321 |
| 6,468,505 | B1 | * | 10/2002 | Lang et al. ............... 424/9.321 |
| 2003/0190284 | A1 | | 10/2003 | Annapragada et al. |

FOREIGN PATENT DOCUMENTS

EP  1121102  8/2001

OTHER PUBLICATIONS

Kao et al. (Acad. Radiol. 2003, 10, 475-483).*
Sachse et al. (Invest. Radiol.1997, 32, 44-50).*
Leike et al. (Invest. Radiol. 2001, 36, 303-308).*
Torchilin et al. (Biochim. Biophys. Acta 1996, 1279, 75-83).*
Kao et al., Long-residence-time nano-scale liposomal iohexol for X-ray-based blood pool imaging, Academic Radiology, May 2003, pp. 475-483.
Leike JU, Sachse A, Rupp K: Characterization of continuously extruded iopromide-carrying liposomes for computed tomography blood-pool imaging. Invest Radiol 2001; 36(6):303-8.
V.P.Torchilin, J.Narula, E.Halpern, B.An Khaw Biochim. Biophys. Acta 1279 (1996) 75-83.
Vera DR, Mattrey RF: A molecular CT blood pool contrast agent. Acad Radiol 2002; 9(7):784-92.
Sachse A, Leike JU, Schneider T, Wagner SE, Rossling GL, Krause W, Brandi M. Biodistribution and computed tomography blood-pool imaging properties of polyethylene glycol-coated iopromide-carrying liposomes. Invest Radiol. Jan. 1997; 32(1):44-50.
Srinath, P. and P.V. Diwan, Stealth liposomes—an overview, Indian J. of Pharmacology 1994, v. 26, pp. 179-184.
Torchilin, V. P., PEG-based micelles as carriers of contrast agents for different imaging modalities, Advanced Drug Delivery Reviews, 2002, v. 54, pp. 235-252.
Written opinion and search report from related PCT Application No. PCT/US05/00876.

* cited by examiner

*Primary Examiner*—Michael G Hartley
*Assistant Examiner*—Melissa Perreira
(74) *Attorney, Agent, or Firm*—Benjamen E. Kern (57) ABSTRACT

Example compositions of liposomes with hydrophilic polymers on their surface, and containing relatively high concentrations of contrast-enhancing agents for computed tomography are provided. Example pharmaceutical compositions of such liposomes, when administered to a subject, provide for increased contrast of extended duration, as measured by computed tomography, in the bloodstream and other tissues of the subject. Also provided are example methods for making the liposomes containing high concentrations of contrast-enhancing agents, and example methods for using the compositions.

19 Claims, 10 Drawing Sheets

COMPOSITIONS AND METHODS FOR ENHANCING CONTRAST IN IMAGING

BACKGROUND

Some medical X-ray imaging techniques provide for detecting variations in contrast of regions of interest of a subject, including different organs, tissues, cells and the like. In order to increase the contrast of regions of interest, some of the imaging techniques may provide for administration of contrast-enhancing agents to the subject. The contrast-enhancing agents may accentuate existing differences in contrast between different areas of interest, or may produce differences in contrast where such differences do not exist without use of the agents.

There have been advancements in medical X-ray imaging, specifically relating to the instruments or machines used to detect the differences in contrast. Such advancements include increases in the speed of such instruments, increases in the resolution of such instruments, and the like. These advancements have provided, in part, for new medical imaging methods. One such method, whole-body imaging, may provide information on the vasculature of the entire body of a subject.

Compared to advances in the instruments used for X-ray imaging, advances in contrast-enhancing agents have not been as forthcoming. Current contrast-enhancing agents for medical imaging using X-rays may have limitations for applications such as whole-body imaging due to, among other things, their rapid clearance from the body, prevalent extravasation, their renal toxicity and their inability to target specific areas of the body.

BRIEF DESCRIPTION OF THE DRAWINGS

In the accompanying drawings, which are incorporated in and constitute a part of the specification, embodiments of contrast-enhancing agent formulations, pharmaceutical compositions containing the formulations, methods for making the formulations and methods for using the formulations in imaging are illustrated which, together with the detailed description given below, serve to describe the example embodiments of formulations, compositions, methods, and so on. It will be appreciated that the embodiments illustrated in the drawings are shown for the purpose of illustration and not for limitation. It will be appreciated that changes, modifications and deviations from the embodiments illustrated in the drawings may be made without departing from the spirit and scope of the invention, as disclosed below.

DETAILED DESCRIPTION

Definitions

Definitions of selected terms or phrases are contained immediately following, and throughout the disclosure. The definitions include examples of various embodiments and/or forms of components that fall within the scope of a term and that may be used for implementation. The examples are not intended to be limiting and other embodiments may be implemented. Both singular and plural forms of all terms fall within each meaning.

"X-ray imaging," as used herein, generally refers to any of a number of procedures using a source producing X-rays. Examples of X-ray imaging include computed tomography and the like.

"Computed tomography" or "CT" or "CAT," as used herein, generally refers to procedures using a rotating X-ray instrument or machine to produce X-ray radiation and direct it through areas of a subject as the instrument rotates. The radiation that is not absorbed by the subject generally is detected and recorded. Generally, the data are sent to a computer which creates detailed cross-sectional images, or slices, of organs and body parts based on differential absorption of X-rays by different areas of the subject.

"Whole body imaging," as used herein, generally refers to methodologies for obtaining images, using CT for example, of the entire body of a subject. In one type of whole body imaging, the entire vasculature system may be examined. Generally, imaging where the vasculature system is examined is called "blood pool imaging."

Description

This application describes example compositions comprising liposomes which contain or are associated with one or more contrast-enhancing agents. In one embodiment, the liposomes contain or are associated with relatively high concentrations of contrast-enhancing agents. In one example, the liposomes contain one or more contrast-enhancing agents for X-ray imaging, CT for example. In one example, the contrast-enhancing agents are not radioactive.

In one embodiment, the liposomes have one or more hydrophilic polymers attached to or associated with the liposomes. In one example, the hydrophilic polymers are attached to or associated with the surface of the liposomes. When administered to a subject, the liposomes may provide increased contrast in the body of a subject. In one example, the increased contrast lasts for an extended period of time.

This application also describes example pharmaceutical compositions that contain the liposomes and contrast-enhancing agents, and example methods of making the compositions of liposomes containing contrast-enhancing agents. The application also describes example methods of using the compositions in X-ray imaging.

Contrast-Enhancing Agents

"Contrast-enhancing agent," as used herein, generally refers to a substance that affects the attenuation, or the loss of intensity or power, of radiation as it passes through and interacts with a medium. It will be appreciated that contrast-enhancing agents may increase or decrease the attenuation. Generally, the contrast-enhancing agents referred to herein increase the attenuation of radiation. In one embodiment, the contrast-enhancing agents described herein are contrast-enhancing agents for X-ray imaging. In one embodiment, the contrast-enhancing agents are used for CT. In one embodiment, the contrast-enhancing agents used herein are nonradioactive. In one embodiment, the contrast-enhancing agents contain iodine.

The contrast-enhancing agents may be classified in various ways. In one classification, for example, iodinated contrast-enhancing agents may be water soluble (e.g., monoiodinated pyridine derivatives, di-iodinated pyridine derivatives, tri-iodinated benzene ring compounds, and the like), water-insoluble (e.g., propyliodone and the like) or oily (e.g., iodine in poppy seed oil, ethyl esters of iodinated fatty acids of poppy seed oil containing iodine, and the like).

In one example, a grouping of iodinated contrast-enhancing agents are water soluble. Present water soluble iodinated contrast-enhancing agents are generally derivatives of tri-iodinated benzoic acid. These compounds may have one or more benzene rings. Such compounds may be ionic or non-ionic. Example ionic compounds include acetrizoate, diatrizoate, iodamide, ioglicate, iothalamate, ioxithalamate, metrizoate, sodium meglumine ioxaglate and others. Example, nonionic compounds include metrizamide, iohexol, iopamidol, iopentol, iopromide, ioversol, iotrolan, iodixanol and others.

Liposomes

"Liposomes," as used herein, generally refer to spherical or roughly spherical particles containing an internal cavity. The walls of liposomes generally are comprised of a bilayer of lipids, particularly phospholipids. There are numerous lipids and phospholipids that can be used to make liposomes. For example, commonly used are amphipathic lipids having hydrophobic and polar head group moieties, and which can form spontaneously into bilayer vesicles in water, as exemplified by phospholipids, or are stably incorporated into lipid bilayers, with its hydrophobic moiety in contact with the interior, hydrophobic region of the bilayer membrane, and its polar head group moiety oriented toward the exterior, polar surface of the membrane.

As used herein, example "phospholipids" include but are not limited to phosphatidic acid (PA) and phosphatidylglycerol (PG), phosphatidylcholine (PC), egg phosphatidylcholine (EPC), lysophosphatidylcholine (LPC), phosphatidylethanolamine (PE), phosphatidylinositol (PI), and phosphatidylserine (PS). The vesicle-forming lipids of this type may be lipids having two hydrocarbon chains, typically acyl chains, and a polar head group. Included in this class are the phospholipids, such as phosphatidylcholine (PC), phosphatidylethanolamine (PE), phosphatidic acid (PA), phosphatidylglycerol (PG), phosphatidylinositol (PI), and sphingomyelin (SM), and others. These phospholipids may be fully saturated or partially saturated. They may be naturally occurring or synthetic. In another example, other lipids that can be included in the liposomes are glycolipids.

The phospholipids used in the example liposomes described herein may be those where the two hydrocarbon chains are between about 14-24 carbon atoms in length, and have varying degrees of unsaturation. Some examples of such phospholipids are given below, in Table 1. Although the phospholipids listed below may be used, alone or in combination with other phospholipids, the list is not intended to be complete. Other phospholipids not listed may also be used.

TABLE 1

| Phospholipids |
| --- |
| 1-Myristoyl-2-Palmitoyl-sn-Glycero-3-Phosphocholine |
| 1-Myristoyl-2-Stearoyl-sn-Glycero-3-Phosphocholine |
| 1-Myristoyl-2-Palmitoyl-sn-Glycero-3-Phosphocholine |
| 1-Myristoyl-2-Stearoyl-sn-Glycero-3-Phosphocholine |
| 1-Palmitoyl-2-Oleoyl-sn-Glycero-3-Phosphate (POPA) |
| 1-Palmitoyl-2-Oleoyl-sn-Glycero-3-Phosphocholine |
| 1-Palmitoyl-2-Oleoyl-sn-Glycero-3-Phosphoethanolamine (POPE) |
| 1-Palmitoyl-2-Oleoyl-sn-Glycero-3-[Phospho-rac-(1-glycerol)] (POPG) |
| 1-Palmitoyl-2-Oleoyl-sn-Glycero-3-[Phospho-L-Serine] (POPS) |
| 1-Palmitoyl-2-Linoleoyl-sn-Glycero-3-Phosphate |
| 1-Palmitoyl-2-Linoleoyl-sn-Glycero-3-Phosphocholine |
| 1-Palmitoyl-2-Linoleoyl-sn-Glycero-3-Phosphoethanolamine |
| 1-Palmitoyl-2-Linoleoyl-sn-Glycero-3-[Phospho-rac-(1-glycerol)] |
| 1-Palmitoyl-2-Linoleoyl-sn-Glycero-3-[Phospho-L-Serine] |
| 1-Palmitoyl-2-Arachidonoyl-sn-Glycero-3-Phosphate |
| 1-Palmitoyl-2-Arachidonoyl-sn-Glycero-3-Phosphocholine |
| 1-Palmitoyl-2-Arachidonoyl-sn-Glycero-3-Phosphoethanolamine |
| 1-Palmitoyl-2-Arachidonoyl-sn-Glycero-3-[Phospho-rac-(1-glycerol)] |
| 1-Palmitoyl-2-Arachidonoyl-sn-Glycero-3-[Phosph-L-Serine] |
| 1-Palmitoyl-2-Docosahexaenoyl-sn-Glycero-3-Phosphate |
| 1-Palmitoyl-2-Docosahexaenoyl-sn-Glycero-3-Phosphocholine |
| 1-Palmitoyl-2-Docosahexaenoyl-sn-Glycero-3-Phosphoethanolamine |
| 1-Palmitoyl-2-Docosahexaenoyl-sn-Glycero-3-[Phospho-rac-(1-glycerol)] |
| 1-Palmitoyl-2-Docosahexaenoyl-sn-Glycero-3-[Phospho-L-Serine] |
| 1-Stearoyl-2-Myristoyl-sn-Glycero-3-Phosphocholine |
| 1-Stearoyl-2-Palmitoyl-sn-Glycero-3-Phosphocholine |
| 1-Stearoyl-2-Oleoyl-sn-Glycero-3-Phosphate |
| 1-Stearoyl-2-Oleoyl-sn-Glycero-3-Phosphocholine |
| 1-Stearoyl-2-Oleoyl-sn-Glycero-3-Phosphoethanolamine |
| 1-Stearoyl-2-Oleoyl-sn-Glycero-3-[Phospho-rac-(1-glycerol] |
| 1-Stearoyl-2-Oleoyl-sn-Glycero-3-[Phospho-L-Serine] |
| 1-Stearoyl-2-Linoleoyl-sn-Glycero-3-Phosphate |
| 1-Stearoyl-2-Linoleoyl-sn-Glycero-3-Phosphocholine |
| 1-Stearoyl-2-Linoleoyl-sn-Glycero-3-Phosphoethanolamine |
| 1-Stearoyl-2-Linoleoyl-sn-Glycero-3-[Phospho-rac-(1-glycerol)] |
| 1-Stearoyl-2-Linoleoyl-sn-Glycero-3-[Phospho-L-Serine] |
| 1-Stearoyl-2-Arachidonoyl-sn-Glycero-3-Phosphate |
| 1-Stearoyl-2-Linoleoyl-sn-Glycero-3-Phosphocholine |
| 1-Stearoyl-2-Arachidonoyl-sn-Glycero-3-Phosphoethanolamine |
| 1-Stearoyl-2-Arachidonoyl-sn-Glycero-3-[Phospho-rac-(1-glycerol)] |
| 1-Stearoyl-2-Arachidonoyl-sn-Glycero-3-[Phospho-L-Serine] |
| 1-Stearoyl-2-Docosahexaenoyl-sn-Glycero-3-Phosphate |
| 1-Stearoyl-2-Docosahexaenoyl-sn-Glycero-3-Phosphocholine |
| 1-Stearoyl-2-Docosahexaenoyl-sn-Glycero-3-Phosphoethanolamine |
| 1-Stearoyl-2-Docosahexaenoyl-sn-Glycero-3-[Phospho-rac-(1-glycerol)] |
| 1-Stearoyl-2-Docosahexaenoyl-sn-Glycero-3-[Phospho-L-Serine] |
| 1-Oleoyl-2-Myristoyl-sn-Glycero-3-Phosphocholine |
| 1-Oleoyl-2-Palmitoyl-sn-Glycero-3-Phosphocholine |
| 1-Oleoyl-2-Stearoyl-sn-Glycero-3-Phosphocholine |
| 1,2-Dimyristoyl-sn-Glycero-3-Phosphate (DMPA) |
| 1,2-Dimyristoyl-sn-Glycero-3-Phosphocholine (DMPC) |
| 1,2-Dimyristoyl-sn-Glycero-3-Phosphoethanolamine (DMPE) |
| 1,2-Dimyristoyl-sn-Glycero-3-[Phospho-rac-(1-glycerol)] (DMPG) |

TABLE 1-continued

Phospholipids 1,2-Dimyristoyl-sn-Glycero-3-[Phospho-L-Serine] (DMPS)
1,2-Dipentadecanoyl-sn-Glycero-3-Phosphocholine
1,2-Dipalmitoyl-sn-Glycero-3-Phosphate (DPPA)
1,2-Dipalmitoyl-sn-Glycero-3-Phosphocholine (DPPC)
1,2-Dipalmitoyl-sn-Glycero-3-Phosphoethanolamine (DPPE)
1,2-Dipalmitoyl-sn-Glycero-3-[Phospho-rac-(1-glycerol)] (DPPG)
1,2-Dipalmitoyl-sn-Glycero-3-[Phospho-L-Serine) (DPPS)
1,2-Diphytanoyl-sn-Glycero-3-Phosphate
1,2-Diphytanoyl-sn-Glycero-3-Phosphocholine
1,2-Diphytanoyl-sn-Glycero-3-Phosphoethanolamine
1,2-Diphytanoyl-sn-Glycero-3-[Phospho-rac-(1-glycerol)]
1,2-Diphytanoyl-sn-Glycero-3-[Phospho-L-Serine]
1,2-Diheptadecanoyl-sn-Glycero-3-Phosphocholine
1,2-Distearoyl-sn-Glycero-3-Phosphate (DSPA)
1,2-Distearoyl-sn-Glycero-3-Phosphocholine (DSPC)
1,2-Distearoyl-sn-Glycero-3-Phosphoethanolamine (DSPE)
1,2-Distearoyl-sn-Glycero-3-[Phospho-rac-(1-glycerol)] (DSPG)
1,2-Distearoyl-sn-Glycero-3-[Phospho-L-Serine]
1,2-Dibromostearoyl-sn-Glycero-3-Phosphocholine
1,2-Dinonadecanoyl-sn-Glycero-3-Phosphocholine
1,2-Diarachidoyl-sn-Glycero-3-Phosphocholine
1,2-Diheneicosanoyl-sn-Glycero-3-Phosphocholine
1,2-Dibehenoyl-sn-Glycero-3-Phosphocholine
1,2-Ditricosanoyl-sn-Glycero-3-Phosphocholine
1,2-Dilignoceroyl-sn-Glycero-3-Phosphocholine
1,2-Dimyristoleoyl-sn-Glycero-3-Phosphocholine
1,2-Dimyristelaidoyl-sn-Glycero-3-Phosphocholine
1,2-Dipalmitoleoyl-sn-Glycero-3-Phosphocholine
1,2-Dipalmitelaidoyl-sn-Glycero-3-Phosphocholine
1,2-Dipalmitoleoyl-sn-Glycero-3-Phosphoethanolamine
1,2-Dioleoyl-sn-Glycero-3-Phosphocholine (DOPC)
1,2-Dioleoyl-sn-Glycero-3-Phosphate (DOPA)
1,2-Dioleoyl-sn-Glycero-3-Phosphocholine (DOPC)
1,2-Dioleoyl-sn-Glycero-3-Phosphoethanolamine (DOPE)
1,2-Dioleoyl-sn-Glycero-3-[Phospho-rac-(1-glycerol)] (DOPG)
1,2-Dioleoyl-sn-Glycero-3-[Phospho-L-Serine] (DOPS)
1,2-Dielaidoyl-sn-Glycero-3-Phosphocholine
1,2-Dielaidoyl-sn-Glycero-3-Phosphoethanolamine
1,2-Dielaidoyl-sn-Glycero-3-[Phospho-rac-(1-glycerol)]
1,2-Dilinoleoyl-sn-Glycero-3-Phosphate
1,2-Dilinoleoyl-sn-Glycero-3-Phosphocholine
1,2-Dilinoleoyl-sn-Glycero-3-Phosphoethanolamine
1,2-Dilinoleoyl-sn-Glycero-3-[Phospho-rac-(1-glycerol)]
1,2-Dilinoleoyl-sn-Glycero-3-[Phospho-L-Serine]
1,2-Dilinolenoyl-sn-Glycero-3-Phosphocholine
1,2-Dilinolenoyl-sn-Glycero-3-Phosphoethanolamine
1,2-Dilinolenoyl-sn-Glycero-3-[Phospho-rac-(1-glycerol)]
1,2-Dieicosenoyl-sn-Glycero-3-Phosphocholine
1,2-Diarachidonoyl-sn-Glycero-3-Phosphate
1,2-Diarachidonoyl-sn-Glycero-3-Phosphocholine
1,2-Diarachidonoyl-sn-Glycero-3-Phosphoethanolamine
1,2-Diarachidonoyl-sn-Glycero-3-[Phospho-rac-(1-glycerol)]
1,2-Diarachidonoyl-sn-Glycero-3-[Phospho-L-Serine]
1,2-Dierucoyl-sn-Glycero-3-Phosphocholine
1,2-Didocosahexaenoyl-sn-Glycero-3-Phosphate
1,2-Didocosahexaenoyl-sn-Glycero-3-Phosphocholine
1,2-Didocosahexaenoyl-sn-Glycero-3-Phosphoethanolamine
1,2-Docosahexaenoyl-sn-Glycero-3-[Phospho-rac-(1-glycerol)]
1,2-Didocosahexaenoyl-sn-Glycero-3-[Phospho-L-Serine]
1,2-Dinervonoyl-sn-Glycero-3-Phosphocholine The liposome composition may be formulated to include amounts of fatty alcohols, fatty acids, and/or cholesterol esters or other pharmaceutically acceptable excipients. For example, the liposomes may include lipids that can stabilize a vesicle or liposome composed predominantly of phospholipids. For example, cholesterol between about 25 to 40 mole percent may be used.

In one embodiment, the type of liposomes used are "sterically stabilized liposomes." Sterically stabilized liposomes generally include a surface that contains or is coated with flexible water soluble (hydrophilic) polymer chains. Such polymer chains may prevent interaction between the liposomes and blood plasma components, the plasma components playing a role in uptake of liposomes by cells of the blood and removal of the liposomes from the blood. Sterically stabilized liposomes may avoid uptake by the organs of the mononuclear phagocyte system, primarily the liver and spleen (reticulendothelial system or RES). Such sterically stabilized liposomes may also be called "long circulating liposomes."

Sterically stabilized liposomes may contain lipids or phospholipids which are derivatized with a polymer chain. The lipids or phospholipids which may be used generally are any of those described above. One exemplary phospholipid is phosphatidylethanolamine (PE) with a reactive amino group which is convenient for coupling to the activated polymers. An exemplary PE is distearyl PE (DSPE).

Examples of polymers which may be suitable for use in sterically stabilized liposomes include the hydrophilic polymers polyvinylpyrrolidone, polymethyloxazoline, polyethyloxazoline, polyhydroxypropyl methacrylamide, polymethacrylamide, polydimethylacrylamide, polylactic acid, polyglycolic acid, and derivatized celluloses, such as hydroxymethylcellulose or hydroxyethylcellulose. Polylysine may be used. Lipid-polymer conjugates containing these polymers attached to a suitable lipid, such as PE, may be used. Other example polymers may be used.

In one embodiment, the polymer in the derivatized lipid or phospholipid is polyethylene glycol (PEG). The PEG may have any of a variety of molecular weights. In one example, the PEG chain has a molecular weight between about 1,000-10,000 daltons. Once a liposome is formed, the PEG chains generally provide a surface coating of hydrophilic chains sufficient to extend the blood circulation time of the liposomes in the absence of such a coating. Such liposomes may be called "PEGylated liposomes." PEGylated liposomes include so-called STEALTH® liposomes, provided by ALZA Corporation.

PEGylated liposomes may also include liposomes with PEG on their surface, where the PEG may be released from the liposome at some time after administration of the liposomes to a subject. In one embodiment, there may be one or more bonds or linkages attaching the PEG, or other hydrophilic polymer, to the liposome surface and/or lipid molecules comprising the liposome surface. In one embodiment, the bonds or linkages may be cleaved, providing for separation of the PEG from the liposome. For example, PEG may be attached to a lipid by one or more disulfide bonds. The disulfide bonds may be cleaved by free thiol, releasing the PEG from the liposome. Other types of cleavable links or bonds may be used to attach the polymers to the liposomes. Other types of agents or compounds may be used to cleave the bonds or linkages.

In one example, the liposomes used have a composition of between about 60 and 75 mole % of one or more of the phospholipids with carbon chains between about 14-24 in length, as described above. A fraction of these phospholipids may be attached to one or more hydrophilic polymers such that between about 1 and 20 mole % of the liposome composition is phospholipid derivatized with polymer chains. In addition, the liposomes used may have between about 25 and 40 mole % cholesterol, or fatty alcohols, fatty acids, and/or other cholesterol esters or other pharmaceutically acceptable excipients, generally for the purpose of stabilizing the liposomes.

In another embodiment, the liposomes may have a molecule or molecules, commonly called a "ligand," accessible from the surface of the liposome, that specifically binds or attaches to, for example, one or more molecules or antigens. Such ligands may direct or target the liposomes to a specific cell or tissue and may bind to a molecule or antigen on or associated with the cell or tissue. The ligand may be an antibody or antibody fragment. The antibody may be a monoclonal antibody or fragment. Such liposomes may be of a type called "targeted liposomes."

In one example, targeted liposomes have lipids or phospholipids which have been modified for coupling antibody molecules to the liposome outer surface. These modified lipids may be of different types. The modified lipid may contain a spacer chain attached to the lipid. The spacer chain may be a hydrophilic polymer. The hydrophilic polymer may typically be end-functionalized for coupling antibody to its functionalized end. The functionalized end group may be a maleimide group, for selective coupling to antibody sulfhydryl groups. Other functionalized end groups may include bromoacetamide and disulfide groups for reaction with antibody sulfhydryl groups, activated ester and aldehyde groups for reaction with antibody amine groups. Hydrazide groups are reactive toward aldehydes, which may be generated on numerous biologically relevant compounds. Hydrazides may also be acylated by active esters or carbodiimide-activated carboxyl groups. Acyl azide groups reactive as acylating species may be easily obtained from hydrazides and permit the attachment of amino containing ligands.

In another embodiment, the phospholipid may be modified by a biotin molecule. To attach the antibody molecule to the biotinylated liposome surface, once the liposome is formed, the antibody molecule may also be modified with biotin and then incubated in the presence of the avidin. Biotinylated lipids, such as biotinylated PE, may be commercially available.

In another example, lipids may be modified by a substrate for use in binding a targeting molecule to a liposome surface. Typically, substrates, as exemplified with biotin, are relatively small, less than about 5,000 daltons for example, to allow their incorporation into multilamellar liposomes with a minimum of disruption of the lipid bilayer structures. The substrate may be one capable of binding irreversibly to a targeting molecule, to ensure that the targeting molecule remains bound to the liposomes over its lifetime in the bloodstream.

Preparation of Liposomes Containing Contrast-Enhancing Agents

The liposomes generally may be prepared by a variety of methods. Example methods include, but are not limited to, hydration of dried lipids, introduction of a volatile organic solution of lipids into an aqueous solution causing evaporation of the organic solution, and dialysis of an aqueous solution of lipids and detergents or surfactants to remove the detergents or surfactants. Additional methods are described in U.S. Pat. No. 5,049,389 by Radhakrishnan, entitled "Novel Liposome Composition for the Treatment of Interstitial Lung Diseases," the descriptions of which are incorporated herein in their entirety by reference.

Liposomes may contain or are associated with one or more contrast-enhancing agents. In one embodiment, the liposomes contain the contrast-enhancing agents. In the process of making liposomes, the contrast-enhancing agents can be added at any desired time. For example, contrast-enhancing agents may be associated with components of liposomes before liposomes are formed. Contrast-enhancing agents may be combined with liposome components at the time the liposomes are made. Contrast-enhancing agents may also be added after the liposomes are formed. Other methods of associating contrast-enhancing agents with liposomes may exist. Generally, contrast-enhancing agents which are hydrophilic in nature are located or associated with the internal cavity of the liposome particles. Contrast-enhancing agents which are lipophilic in nature generally are located or associated with the lipid bilayer of liposome particles. Generally, the contrast-enhancing agents herein are located or associated with the internal cavity of the liposome. The example liposomes may contain at least 30 mg iodine/milliliter (I/ml) of liposome suspension when iodinated contrast enhancing agents are used.

Figure 1:
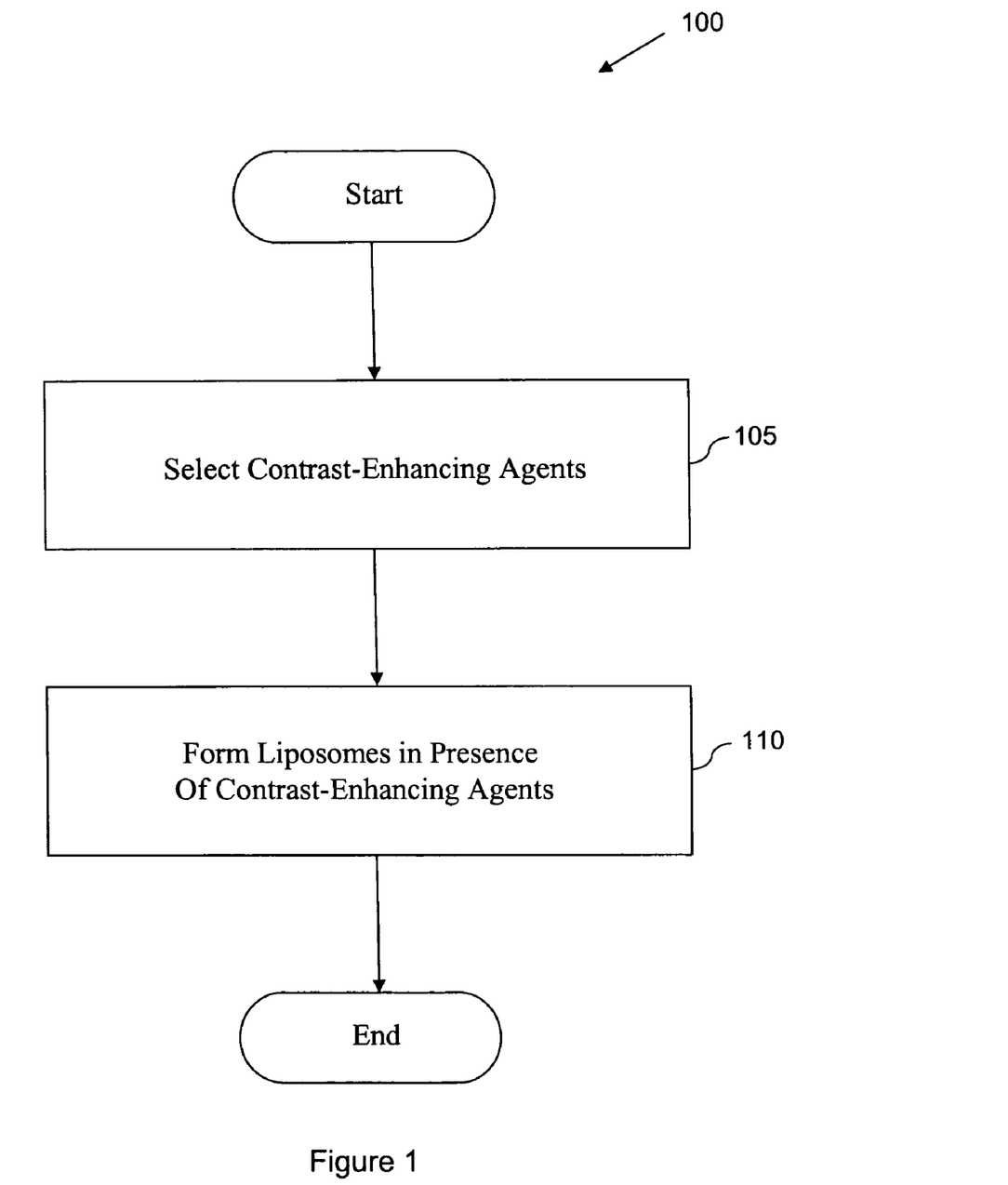
FIG. 1 illustrates an example method 100 of preparing liposomes containing or associated with contrast-enhancing agents.

There are a variety of methods known in the art for loading the contrast-enhancing agents into the liposomes. For example, in passive loading, liposomes are formed in a solution of the contrast-enhancing agent to be used. Illustrated in FIG. 1 is one example method 100 that may be performed by selecting one or more contrast-enhancing agents to be used (block 105) and forming liposomes in the presence of the one or more contrast-enhancing agents (block 110). Generally, the methods described earlier for preparing liposomes may be used. Such methods include hydration of dried lipids, introduction of a volatile organic solution of lipids into an aqueous solution causing evaporation of the organic solution, dialysis of an aqueous solution of lipids and detergents or surfactants to remove the detergents or surfactants, and others.

Figure 2:
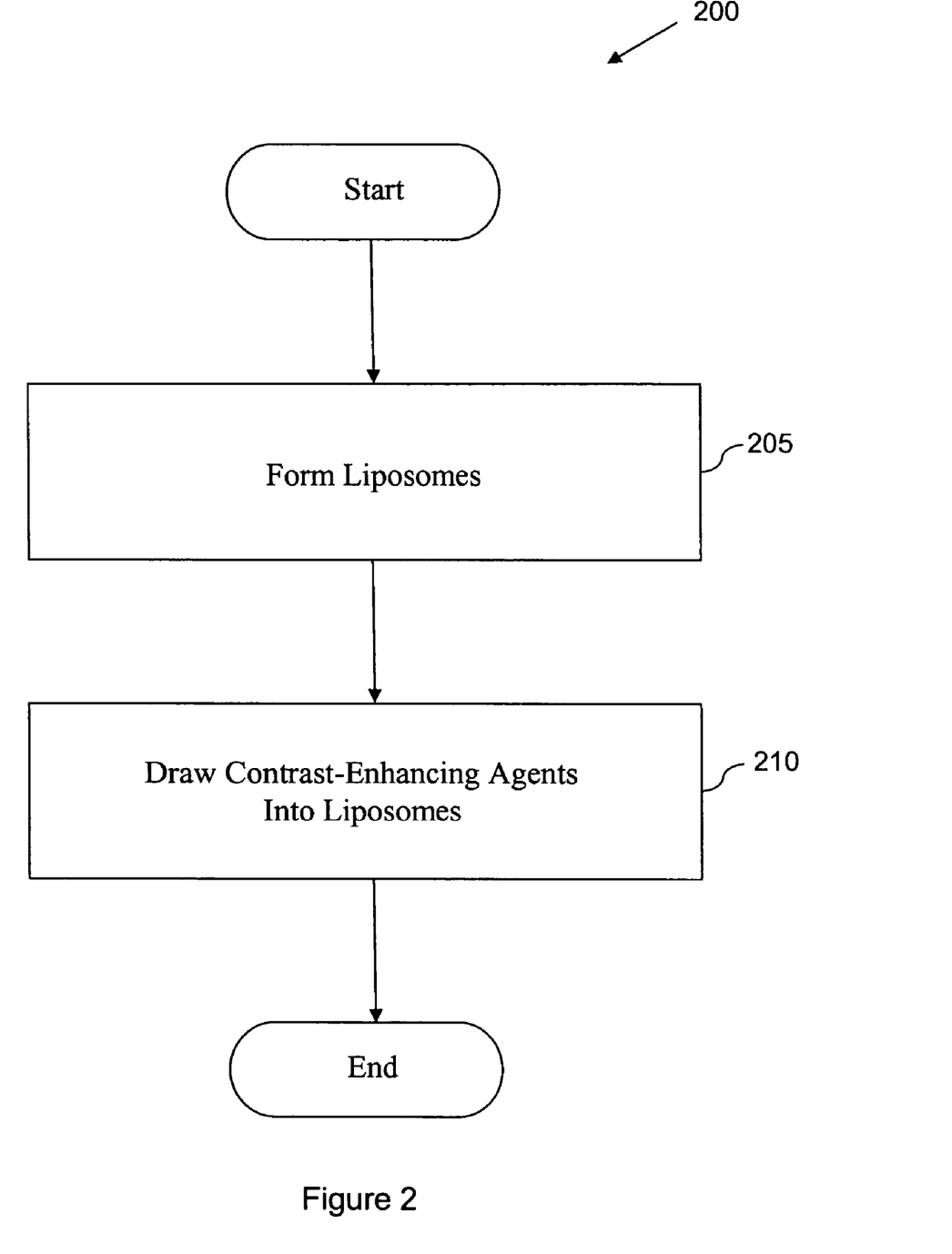
FIG. 2 illustrates another example method 200 of preparing liposomes containing or associated with contrast-enhancing agents.

In active or remote loading, a variety of methods can be used. Generally, in these methods, the agent to be encapsulated by the liposomes (i.e., contrast-enhancing agents) is drawn or attracted into liposomes, or trapped or contained in liposomes as they are formed. In one example, FIG. 2 illustrates a method 200 that may be performed by forming liposomes (block 205) and drawing one or more contrast-enhancing agents into the liposomes (block 210). In one approach, an ion gradient may be established from the interior to the exterior of the liposome, and used to promote encapsulation of the desired active agent. In a common application of this technique, ammonium sulfate may be passively encapsulated in liposomes. Upon substitution of the external phase with a suitable (neutral pH) buffer, the ammonia may diffuse out of the liposome, while leaving behind the charged protons and sulfate ions. Neutral molecules of the active agent (i.e., contrast-enhancing agent) then may diffuse into the liposomes, down the concentration gradient, and are protonated, and possibly sulfated by the internal ions (see for example, Ceh and Lasic, 1997, J. Colloid Interface Sci., 185:9-18). In another embodiment of this approach, calcium acetate rather than ammonium sulfate may be the loading agent.

In another type of active loading, called pH based loading, a proton may be dissociated from the contrast-enhancing agents, causing the contrast-enhancing agents to enter into and remain in the liposomes (see Ceh and Lasic, 1997, J. Colloid Interface Sci., 185:9-18). In still another method, a chelating agent within the liposome may result in trapping of contrast-enhancing agents therein as well as further diffusion of contrast-enhancing agents into the liposomes (see Patent No. WO0023052 by Colbern, Working and Slater, entitled "Liposome-Entrapped Topoisomerase Inhibitors").

After the loading of contrast-enhancing agents into liposomes, steps may be used to remove contrast-enhancing agents that have not been loaded and are not associated with liposomes, or other impurities. Such steps may comprise techniques such as ion exchange, diafiltration, washing of the liposomes using ultracentrifugation, dialysis, and the like.

After liposomes are made, techniques for manipulating the liposomes may be used. For example, a preparation of liposomes made by standard techniques may vary in size and lamellarity (i.e., wall thickness) after it is made. Techniques such as subjecting the liposomes to a high shearing force, extrusion of the liposomes through membranes, or sonication of the liposomes may be used either to select liposomes of a desired size or modify the liposomes such that they have a desired size. After manipulation of liposomes by these methods, the size distribution of the liposomes may be measured to ensure that liposomes of the desired size have been obtained. Techniques such as Fraunhofer diffraction and dynamic light scattering (DLS) may be used to measure the size distribution of the liposomes. Such techniques generally measure an equivalent spherical diameter which, in the case of Fraunhofer diffraction, may be the diameter of a sphere with the same light scattering properties as the measured liposomes. In the case of DLS, equivalent spherical diameter may be the diameter of a sphere with the same diffusion coefficient as the measured liposomes. Generally, the example liposomes have an average diameter of less than 150 nm. Example preparations of liposomes may have an average diameter of approximately 120 nm or less. Example preparations of liposomes may have an average diameter of approximately 100 nm or less. It will be appreciated that other sizes can be used.

In one embodiment, a nano-scale liposomal formulation carrying over 30 mg of iohexol per ml of liposome can be formulated using passive loading. In this formulation, the lipid composition of the bilayer has been adjusted as described below to allow this amount of contrast-enhancing agent to be encapsulated. In one example, it has been found that by using pure DPPC (1,2-dipalmitoyl-sn-glycero-3-phosphatidylcholine) of C16 chain length, with about 40 mole % cholesterol and 5 mole % mPEG-DSPE (N-(carbonylmethoxypolyethyleneglycol 2000)-1,2-distearoyl-sn-glycero-3-phosphatidylethanolamine) (the polyethylene glycol-conjugated lipid that confers long circulating properties), the encapsulation of active molecules inside the liposomes may be increased by 20% over what is possible using hydrogenated Soy PC(HSPC), a mixture of C16 and C18 lipids, or pure DSPC (1,2-distearoyl-sn-glycero-3-phosphocholine) of C18 chain length. Using a formulation of 55 mole % DPPC, 40 mole % cholesterol and 5 mole % mPEG-DSPE and an iohexol solution of 350 mg I/ml, an overall concentration of over 30 mg I/ml has been achieved, with an average liposomal diameter of 100.6±3 nm, as determined by DLS.

Pharmaceutical Compositions and Administration to Subjects

The liposomes containing or associated with one or more contrast-enhancing agents may be part of a pharmaceutical composition suitable for administration to a subject. The compositions generally are administered using a route that delivers the composition to an area of interest. In one example, the compositions of contrast-enhancing agents are administered parenterally to the subject, such as through intravenous, intraarterial, subcutaneous or other route of injection.

The formulation of the particular pharmaceutical composition generally will depend on the method by which the composition is administered to a patient. It will be appreciated that the pharmaceutical compositions can include salt, buffering agents, preservatives, other vehicles and, optionally, other agents. Compositions suitable for parenteral administration may comprise a sterile, pyrogen-free, aqueous or oleaginous preparation which is generally isotonic with the blood of the subject. This aqueous preparation may be formulated according to known methods using suitable dispersing or wetting agents and suspending agents. The sterile injectable preparation also may be a sterile injectable solution or suspension in a non-toxic parenterally-acceptable diluent or solvent. Among acceptable vehicles and solvents that may be employed are water, Ringer's solution, and isotonic sodium chloride or other salt, dextrose, phosphate buffered saline and the like, or combinations thereof.

The pharmaceutical compositions used may also contain stabilizers, preservatives, buffers, antioxidants, or other additives. In addition, sterile, fixed oils may be employed as a solvent or suspending medium. In addition, fatty acids such as oleic acid may be used in the preparation of injectables. Carrier formulations suitable for the administrations may be found in Remington's Pharmaceutical Sciences, Mack Publishing Co., Easton, Pa. The pharmaceutical compositions may conveniently be presented in unit dosage form.

Parenteral administration contemplates the use of a syringe, catheter or similar device, which delivers the pharmaceutical composition to a site. Delivery may result, at least initially, in the pharmaceutical composition being systemically distributed throughout the circulatory system of the subject.

Generally, the pharmaceutical compositions may be administered to the subject at a point in time before the imaging of the subject is performed. The amount of the pharmaceutical compositions administered preferably results in increased contrast of one or more tissues of the subject. Ultimately, the attending physician or technician generally will decide the amount of pharmaceutical composition to administer to the subject. Generally, the increase in contrast can be any level above what is present without use of the contrast-enhancing agents in the pharmaceutical compositions. Example increases in contrast of at least 50 HU, at least 100 HU or more, to one or more organ systems, including the vasculature, may be obtained.

Applications

The compositions of liposomes containing contrast-enhancing agents or pharmaceutical compositions thereof, when administered to a subject, may maintain a level of contrast-enhancing agent in the blood and/or organs of a subject that results in an increased contrast and is detectable by X-ray imaging techniques. The increase in contrast may be detectable for an extended period of time. Depending on the particular application, the compositions described herein may have half lives in the circulation of from minutes to hours, to even days. In one example, half lives in the circulation of from 8 to 24 hours can be obtained. In one example, an administered composition provides an enhanced contrast that remains detectable at least 30 minutes after administration. In another example, an administered composition provides an enhanced contrast that remains detectable at least 5 minutes after administration. Many applications, including those in anatomic, functional and molecular imaging may be possible. For example, use of the compositions described herein may have applications in cardiology, oncology, neurology and other areas.

In one embodiment, blood pool imaging may be used to detect and, in some cases, quantify ischemia. For example, because injection of the pharmaceutical compositions generally alters the contrast of the entire vasculature, reduced blood flow as is present in ischemia may be detected. A variety of types of ischemia may be detected, including that causing ischemic bowel disease, pulmonary embolism, and types of ischemia that produce cardiomyopathy, and others. In other applications, aneurysms may also be detected.

In one embodiment, the compositions described herein may be used in cardiac imaging to detect, examine and/or assess stenosis, and the therapy or remediation of stenosis, as occurs in angioplasty, for example. The utility of such techniques may be enhanced through the use of contrast-enhancing agent preparations, such as those described herein.

In one embodiment, the compositions described herein may be used to detect myocardial microcirculatory insufficiencies. Myocardial microcirculation is known to display signs of obstruction before the epicardial arteries show signs of obstruction. Therefore, detection of obstruction in the myocardial microcirculation may be an earlier detector of atherosclerosis in presymptomatic, at-risk patients, than conventional methods. The compositions described herein may facilitate detection of obstructions in the myocardial microcirculation.

In another embodiment, the compositions described herein may be used to detect and characterize a wide range of tumors and cancers. These applications may be facilitated by the property of sterically stabilized liposomes being present for extended periods of time in the circulation and to extravasate at regions where the vasculature is "leaky," such as in tumors, for example. The leakiness of the vasculature in tumors may be attributed to the high proportion of neovasculature, the result of continuing angiogenesis as the tumor grows in size. Upon encountering such leaky vasculature, liposomes may leave the circulation, driven with the extravasate fluid, by hydrostatic pressure. Such liposomes generally do not return to the circulation after extravasation since the pressure gradient opposes such return. Such methods can be used to detect both primary and metastatic tumors.

In other embodiments, the compositions may be used for "staging" or classification of tumors. Such applications may depend on, among other things, differences in the "leakiness" of the vasculature of a given tumor or cancer at different stages of progression.

In one embodiment, the compositions may be used in the area of monitoring and characterizing injury and healing of damaged spinal cords. In a typical spinal cord injury, as occurs in an automobile accident for example, there may also be damage to tissue surrounding the spinal cord. It is thought that the process of healing of the surrounding tissue may be deleterious to healing of the spinal cord. It is thought that formation of neovasculature in the surrounding tissue, as occurs in healing of the surrounding tissue, may inhibit healing of the spinal cord. It is thought that by inhibiting healing of the surrounding tissue, and the formation of neovasculature in the surrounding tissue, the spinal cord may heal. Subsequently, the surrounding tissue may heal. The compositions of contrast-enhancing agents described here may be useful for monitoring the healing and inhibition of healing of the tissue surrounding the spinal cord.

There may be a variety of other applications for the compositions described herein. For example, the compositions may be used in detection and monitoring of inflammation, reperfusion injuries, and the like.

Additionally, the liposomes which comprise the compositions of contrast-enhancing agents may be targeted to desired cells and tissues in the body of a subject by, for example, attaching antibodies to the surface of the liposomes. Such targeting may result in enhanced contrast to the targeted areas of the body.

The compositions of contrast-enhancing agents may have a relatively long residence time in the body, low extravasation, except in those areas of the vasculature that are leaky as described above, may be relatively nontoxic to the kidneys and may be used to target specific areas of the body. Additionally, the traditional osmolality related toxicity problems associated with ionic contrast-enhancing media generally are not an issue with the liposomal encapsulates since the high osmolality phase is interior to the liposomes and generally is not exposed to the blood.

EXAMPLES

Example 1

Preparation of PEGylated Liposomes Containing Iohexol

Example liposomal iohexol formulations can be produced as follows. Briefly, a lipid mixture (200 mM) of 1,2-Dipalmitoly-sn-glycero-3-phosphocholine (DPPC), cholesterol (chol) and N-(carbonyl-methoxypolyethyleneglycol 2000)-1,2-distearoyl-sn-glycero-3-phosphoethanolamine (DSPE-MPEG2000), in a 55:40:5 molar ratio, was dissolved in ethanol at 65° C. The ethanol solution was then hydrated with iohexol (350 mg I/ml) for 1.5-2 hours. Liposomes were extruded on a 10 ml Lipex Thermoline extruder (Northern Lipids, Vancouver, British Columbia, Canada) with 5 passes through a 0.2 µm Nucleopore membrane (Waterman Inc., Newton Mass.) and 7 passes through a 0.1 µm Nucleopore membrane (Waterman Inc., Newton Mass.). Liposomes were then be dialyzed in a 300,000 molecular weight cutoff (MWCO) dialysis bag against phosphate buffer saline (PBS) overnight to remove the free iohexol.

The size of the resulting example liposomal iohexol formulations can be determined by dynamic light scattering (DLS) using a modified BI-90 goniometer, a JDS uniphase 532 nm laser, Hamamastu photomultiplier and Brookhaven DLS Software Version 3.16. The average diameter of the liposomal iohexol capsules was 100.6 nm (STD=3.0 nm), which is in nano-scale range, as determined by DLS.

The iohexol concentrations of example liposomal iohexol formulations can be determined by measuring the absorption at 245 nm using a UV-Vis spectrophotometer. Equivalent iodine concentrations can then be calculated. In the example preparations, different lipid hydration times (1.5 hours and 2 hours) resulted in different iohexol loading concentrations (30 and 34.8 mg I/ml respectively). The 30 mg I/ml iohexol liposomal formulation was used in the in vitro stability tests described below, and the 34.8 mg I/ml iohexol liposomal formulation were used in the in vivo CT imaging experiment described below.

The osmolarity of liposomal iohexol formulation can be measured by, for example, Vapro® vapor pressure osmometer (Wescor Inc.). The osmolarity of the example iohexol formulations ranged between 305 to 315 mmol/kg.

Example 2

In Vitro Stability of PEGylated Liposomes Containing Iohexol

The in vitro stability of example liposomal iohexol formulations can be determined by measuring the leakage of iohexol from liposomal iohexol formulations both in PBS at 4° C. and in plasma at 37° C. In the procedure, 1 ml of an example liposomal iohexol formulation was placed in a 300,000 MWCO dialysis bag and dialyzed against 250 ml PBS at 4° C. At each time point (0, 1, 2, 3, 8, 24 hours, and 3, 4, 5, 6, 8, 10, 18 days), 1 ml of the dialysate was removed for a UV absorption-based iohexol measurement. At least three data points were obtained at each time point. After measurement, samples were returned to the PBS to maintain constant volume.

To measure stability in plasma, the example liposomal iohexol formulations can be dialyzed against 250 ml PBS at 25° C. for 1 hour to remove the free iohexol. In these experiments, 1 ml liposomal iohexol formulations was placed in a 300,000 MWCO dialysis bag with 4 ml of human plasma, and dialyzed against 250 ml PBS at 37° C. (1:4 ratio was chosen). One ml of the external phase was removed at 0, 1, 2, 3, 4, 5, 6 and 8 hours respectively, and analyzed by the UV-vis absorption. Since plasma components also leak from the dialysis bag and have a finite absorbance at 245 nm, a control experiment, where a PBS-plasma mixture is dialyzed against PBS, was also performed. The absorbance of the external phase was subtracted from that for the liposomal iohexol formulation experiments and the resulting absorbance traces can be representative of the leakage of iohexol from liposomal iohexol formulations. The results showed that the liposomal iohexol formulation was stable in PBS and in human plasma.

Figure 3:
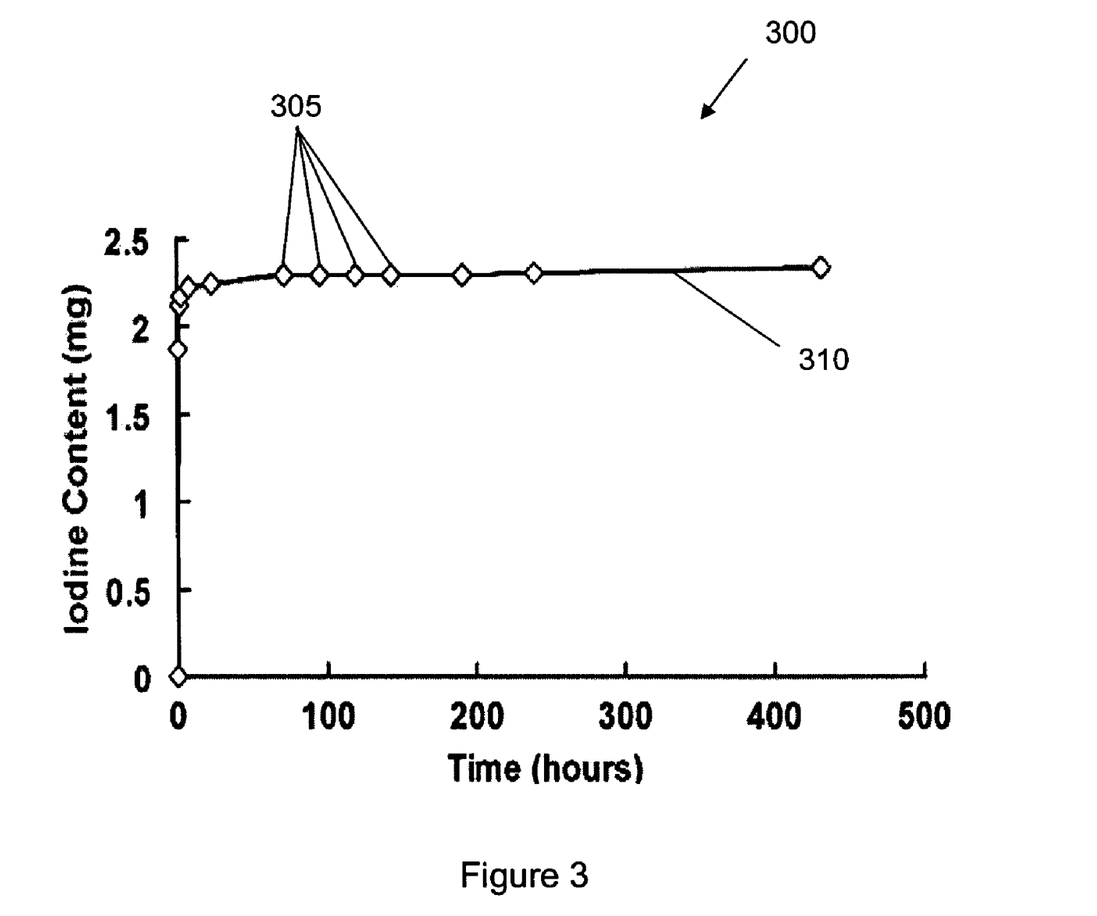
FIG. 3 shows an example in vitro stability test 300 of one embodiment of a liposomal iohexol formulation when dialyzed with PBS at 4° C. The total iodine amount is 30 mg iodine.

The example leakage curves of iohexol 300 is shown in FIG. 3. The example liposomal iohexol formulation (30 mg I/ml) was dialyzed against 250 ml of PBS at 4° C. At example time points 305 of 0, 1, 2, 3, 8, 24 hours, and 3, 4, 5, 6, 8, 10 and 18 days, the dialysate was tested for the amount of iohexol. The example leakage curve 310 was obtained by drawing a line through the data at each time point. The data show that the curve stabilized after 1 hour of dialysis. Liposomal iohexol exhibited a leakage of 7.4% of the total encapsulated iohexol over 8 hours, and 7.8% for 18 days by equilibrium dialysis at 4° C. The shelf life of liposomal iohexol formulation therefore can be longer than 18 days.

Figure 4:
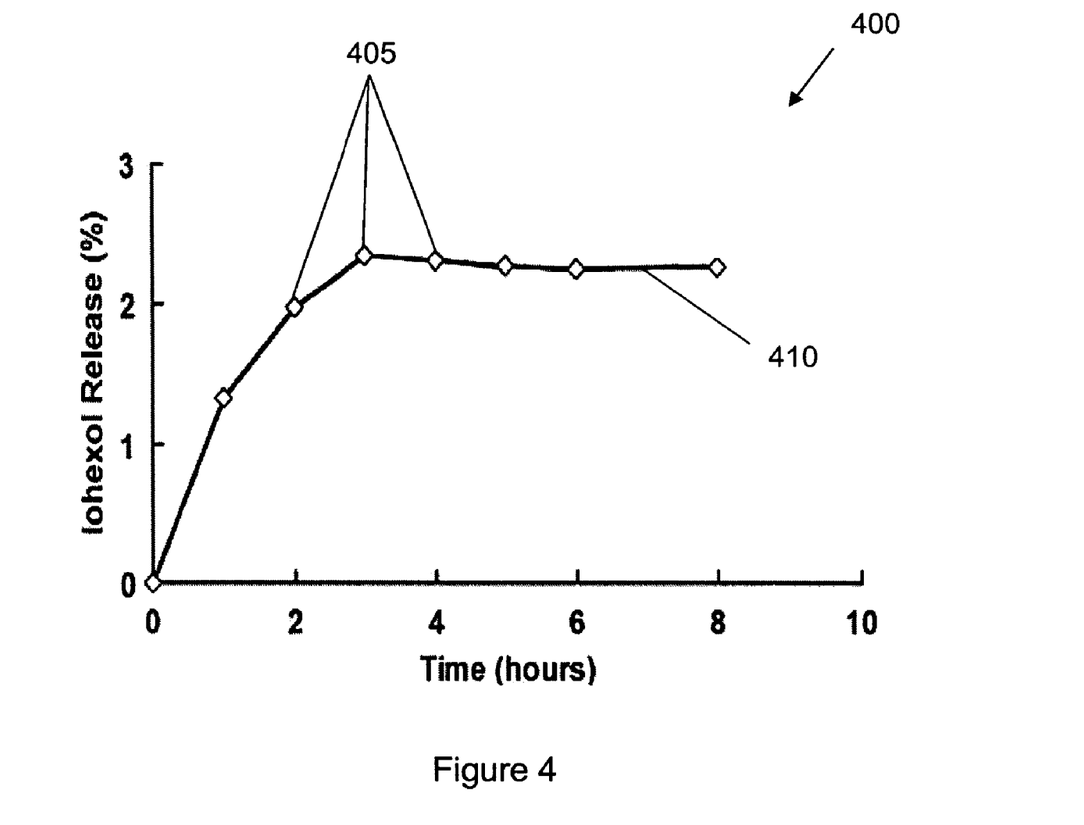
FIG. 4 shows an example in vitro plasma stability test 400 of one embodiment of a liposomal iohexol formulation when dialyzed against PBS at 37° C. The total iodine content is 28 mg iodine.

The leakage curves of an example iohexol-plasma mixture 400 is shown in FIG. 4. Liposomal iohexol that had previously been dialyzed against PBS for 1 hour was used in this study to determine the contribution of plasma to leakage of iohexol from the liposomes. At example time points 405 of 0, 1, 2, 3, 8, 24 hours, and 3, 4, 5, 6, 8, 10 and 18 days, the dialysate was tested for the amount of iohexol. The example leakage curve 410 was obtained by drawing a line through the data at each time point. The data show that the curve stabilized after 3 hours, and the liposomal iohexol formulation exhibited a leakage of 2.3% of the total encapsulated iohexol for the 8 hour period, beyond the leakage observed during storage in PBS. Together, these results indicate that the liposomal iohexol formulation can be about 90% encapsulated when stored for 18 days and then injected.

Example 3

In Vivo Studies Using Imaging of PEGylated Liposomes Containing Iohexol in a Rabbit A female rabbit weighing 2.2 kg was anesthetized with 35 mg/kg ketamine and 5 mg/kg xylazine given intramuscularly, followed by 2% isoflurane vapor given by face cone. After tracheal intubation and placement of venous catheter in an ear vein, 20 mg pentobarbital was given intravenously. The animal's lungs were ventilated using a pressure control ventilator set to peak airway pressure of 15 cm $H_2O$, and 25 breaths $min^{-1}$. After transport to the CT scanner, the animal was given 0.25 mg of pancuronium (muscle relaxant) to insure minimal motion during the image acquisition. Supplemental pentobarbital was given every 30-60 minutes, 10-20 mg per dose. An initial volume image of the chest and abdomen was obtained using a 4 slice Phillips MX8000 MDCT scanner in spiral scanning mode, (100 mAs, 120 keV) with a single slice equivalent pitch of 1.25, and a slice collimation and thickness of 1.3 mm. Images were reconstructed into a 512×512 matrix using a standard reconstruction kernel (the "B" kernel). A 0.5 second gantry rotation speed was used. During each imaging protocol, the rabbit was held apneic with airway pressure fixed at 20 cm $H_2O$ (e.g. near total lung capacity) using an underwater bubbler tube on the exhalation port. Next, 15 ml of 34 mg I/ml liposomal iohexol formulation was hand-injected followed by a repeat volume image, then a second injection of 15 ml of liposomal iohexol formulation suspension was followed by a third volume image. A total dose of 475 mg iodine per kg was given in the two injections. Repeat volume images were then initiated at approximately 12, 60, 90, 120, 150 and 180 minutes after the second contrast injection. Following the last image acquisition (~3.5 hr post injection of contrast agent), the animal was euthanized with an overdose of pentobarbital and a final, high resolution image was obtained with no motion artifact (with the same airway pressure and image acquisition settings). Finally, an ultrahigh resolution scan was obtained using an ultra sharp reconstruction kernal ("D" kernal and a 1024×1024 image matrix) to evaluate anatomic detail without the presence of cardiogenic motion.

Example 4

Image Reconstitution

Subsequent offline example reconstructions were performed for each of the scans obtained as described in Example 3 with the smallest field of view (5 cm×5 cm, 0.1 mm voxel size) for 3° D. viewing of the heart. The enhanced heart chambers were visualized by selecting appropriate settings of the volume rendering software present on the Philips MXV workstation software (version 4.1). Once the settings were established, the same rendering and display settings were used for all time points. Additional structures were segmented at various time points.

Quantitative analysis was performed by locating regions of interest (ROI) in the aorta, heart, kidney (core and cortex), liver, muscle and spleen. Mean Hounsfield units (HU) were determined at each time point to enable tracking of any decay in contrast concentration with time in each of these structures. Slice and slice location of the ROI's were adjusted for minor variations in anatomic configuration of the rabbit from time point to time point.

Example 5

Time-Attenuation of PEGylated Liposomes Containing Iohexol In Vivo

Figure 5:
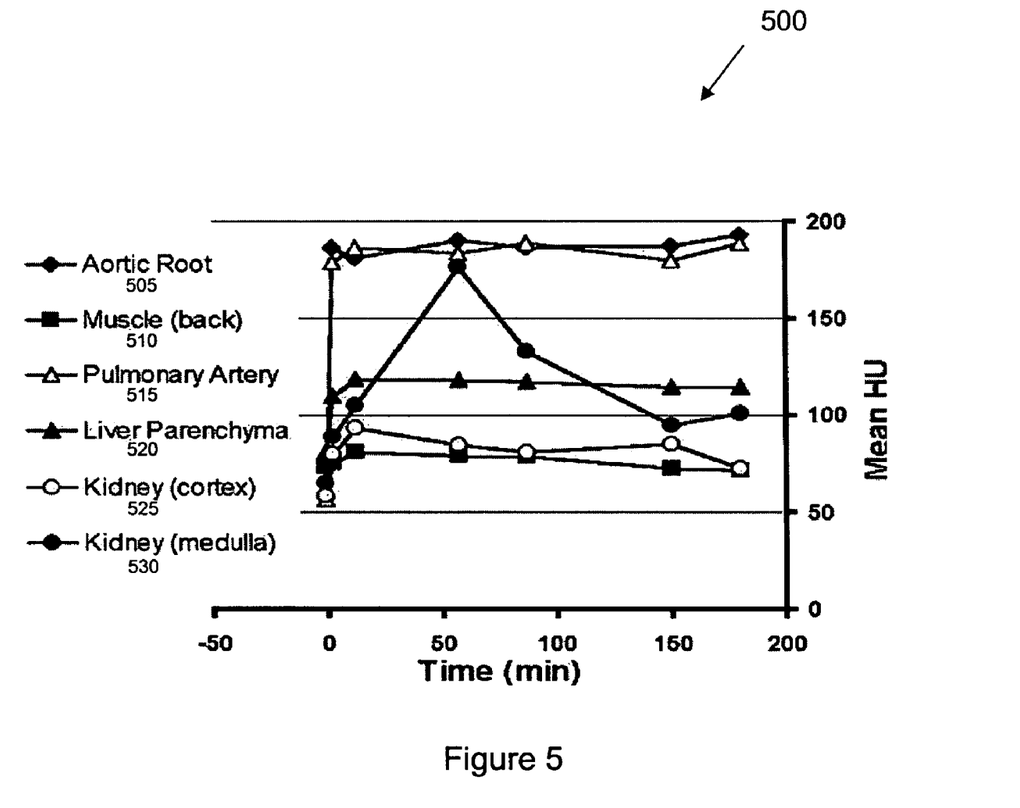
FIG. 5 shows example time-attenuation curves 500 of various regions of interest at different post-injection times after intravenous administration of one embodiment of a liposomal iohexol formulation (injection to 2.2 kg rabbit vein at a dose of 475 mg I/kg) given in two incremental injections.
Figure 6:
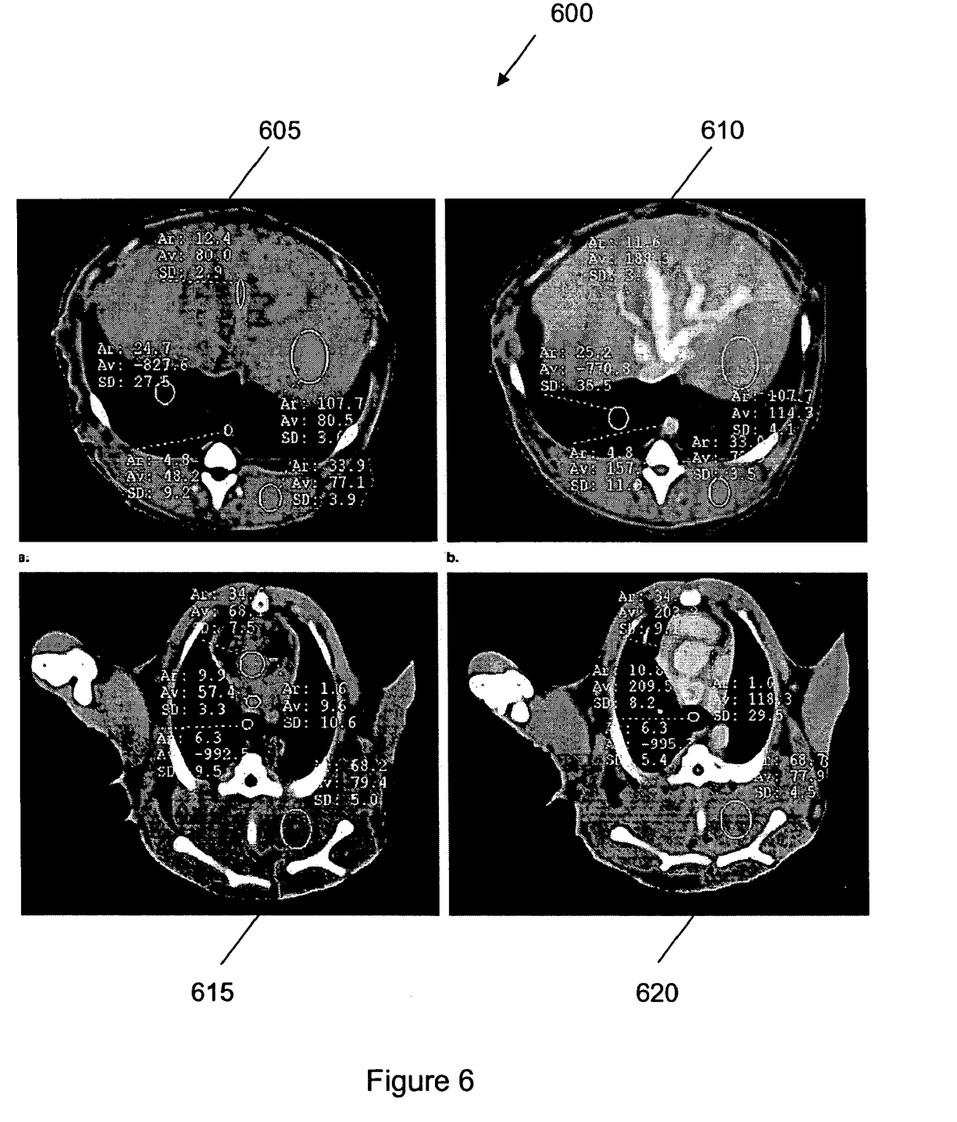
FIG. 6 shows example pre- and post-enhancement computed tomography (CT) images 600 of one embodiment of liposomal iohexol: 2.2 kg rabbit with 34.8 mg/ml iodine IV injection. Left Panels 605, 615: pre-contrast; Right Panels 610, 620: 2 hours 18 minutes post injection. Upper panels 605, 610 are images taken at the level of the liver. Lower panels 615, 620 are images taken at mid heart level.

The example image analysis described in Example 4 was performed at regions of interest in the aorta, kidney (medulla and cortex), liver parenchyma, back muscle, left main coronary artery, pulmonary artery, and in the main stem bronchus (as a control value) and plotted over time in a graph 500 (FIG. 5). Mean attenuations (Hounsfield units) were determined at the time points stated in Example 3 to quantify the decay in contrast with time in each of these locations. The data show the enhancement and maintenance of contrast over time in various regions of interest. The average attenuation in the aorta 505, pulmonary artery 515 and liver cortex 3.5 hours post contrast injection attenuation was 200 HU (enhancement 130 HU), and in the kidney cortex 525 the attenuation was 75 HU (enhancement 25 HU). Attenuation in the blood pool rose rapidly post-injection, and remained virtually constant for the 3.5 hours of study. A slight increase in attenuation in the liver parenchyma 520 was observed. A transient increase in the kidney core 530 was observed, indicating early clearance with little to no clearance later in the study. The small region of interest placed over the left main coronary artery indicated attenuation of 9 HU at base line and peaked at a value of 118 HU. FIG. 6 shows 0 hour baseline 605 and peak enhanced 610 images obtained 2 hours 18 minutes post liposomal injection at the level of the liver. FIG. 6 also shows 0 hour baseline 615 and peak enhanced 620 images obtained 2 hours 18 minutes post liposomal injection at the level of the mid-heart.

These data indicate the residence time of example PEGylated liposome formulations, which provided contrast enhancement, to be more than 3 hours. Additionally, the data show that contrast enhancement in muscle can be low, indicating the liposomal iohexol can be retained in the blood vessels and does not rapidly extravasate. Additionally, the contrast enhancement in the liver parenchyma indicated that clearance of the composition may substantially be due to the liver, and not the kidneys.

Example 6

Figure 7:
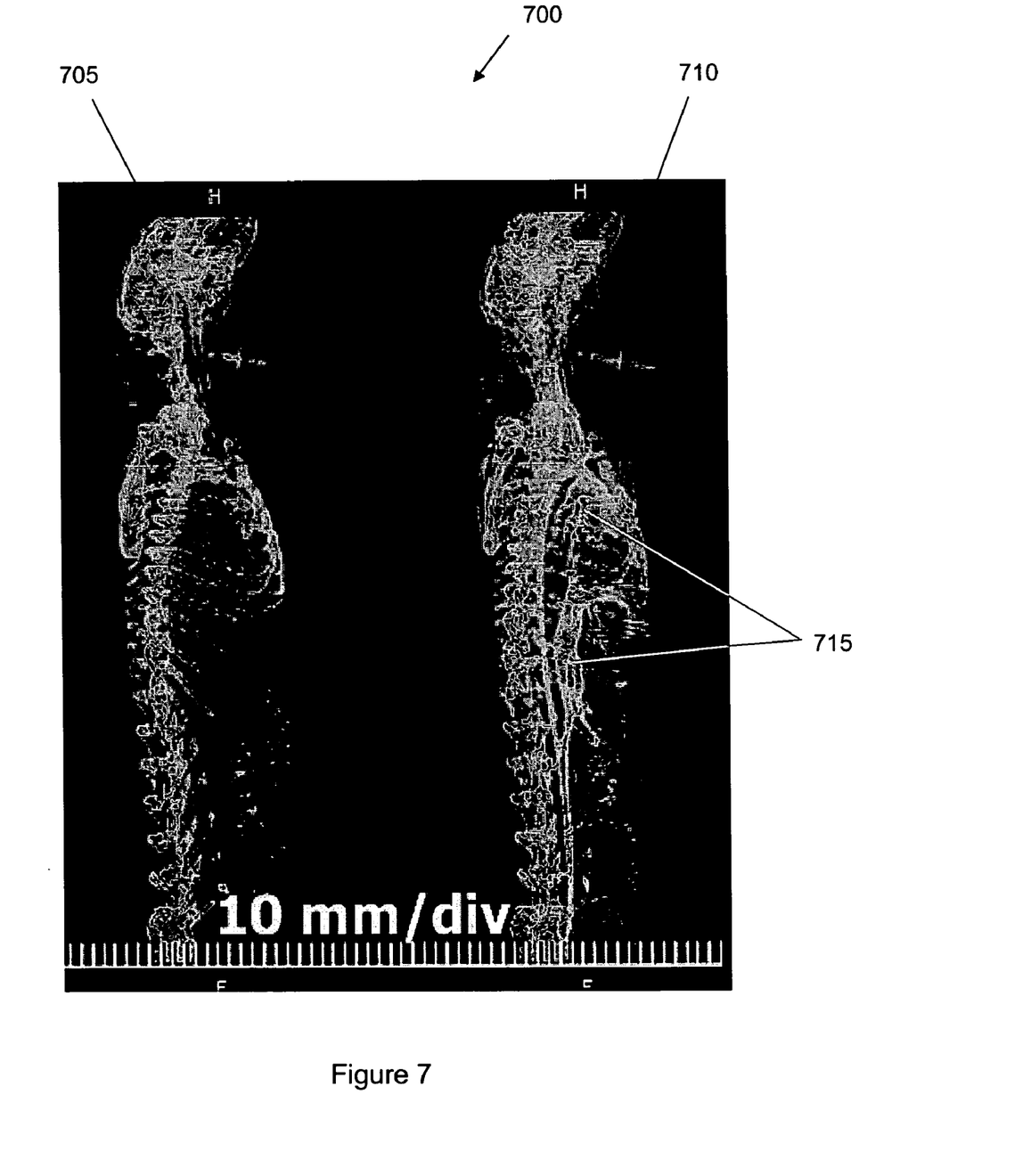
FIG. 7 shows example volume-rendered CT images of a rabbit torso 700. Left panel 705: right lateral view before contrast injection; Right panel 710: right lateral view 2 hours 18 minutes after injection of 475 mg I/kg of one embodiment of a liposomal iohexol formulation. Note the enhanced vascular bed seen in the right panel 715.
Figure 9:
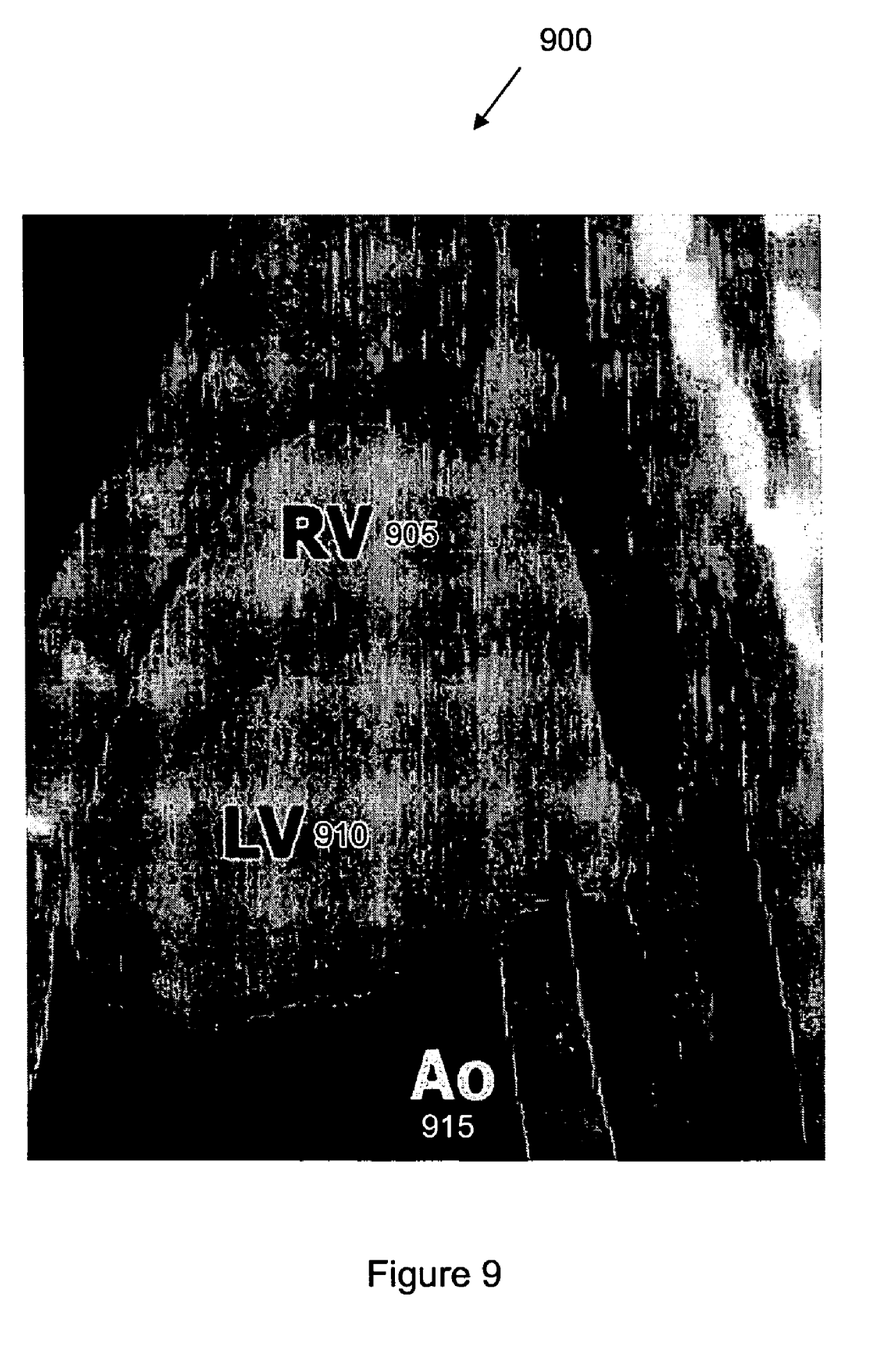
FIG. 9 shows an example of a thick-slab rendering of ultra-high resolution CT scan (24 line pair per cm) of post-mortem rabbit (no cardiac motion) 900. Rabbit was sacrificed 3.5 hours after the second injection of one embodiment of liposomal iohexol. Images were reconstructed to fit a 1,024× 1,024 matrix with a 0.5-cm field of view.
Figure 10:
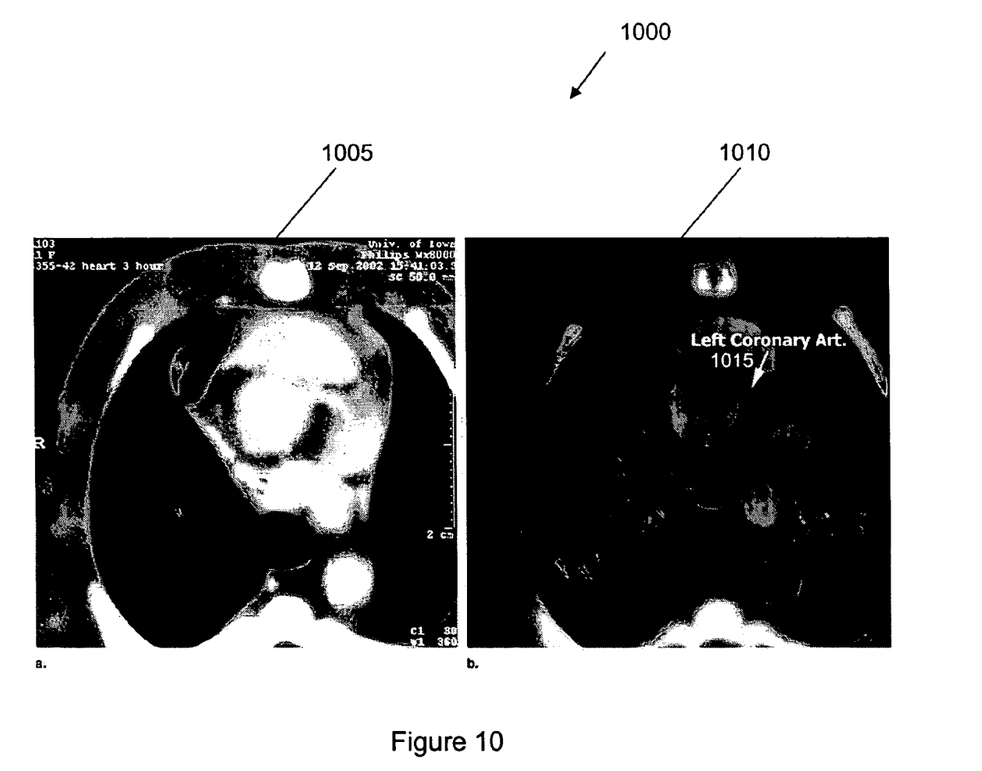
FIG. 10 shows an example image of the left coronary artery of the rabbit under high magnification 1000.

In Vivo Images of Heart after Administration of PEGylated Liposomes Containing Iohexol Additionally, example images of the rabbit heart were analyzed 700 (FIG. 7), 800 (FIG. 8), 900 (FIG. 9) and 1000 (FIG. 10). FIG. 7 shows volume rendered images of the whole rabbit, before 705 and 2 hours 18 minutes after injection of the liposomal iohexol formulation 710. Enhancement to the vasculature 715 due to the liposomes can be seen. The results show that, even more than 2 hours after injection, the blood vessels can be visible 715 while, using the same display and rendering parameters, they may not be visible before liposome administration. This enhancement can persist up until the time that the animal is euthanized at more than 3 hours after injection of the second dose of liposomes.

Figure 8:
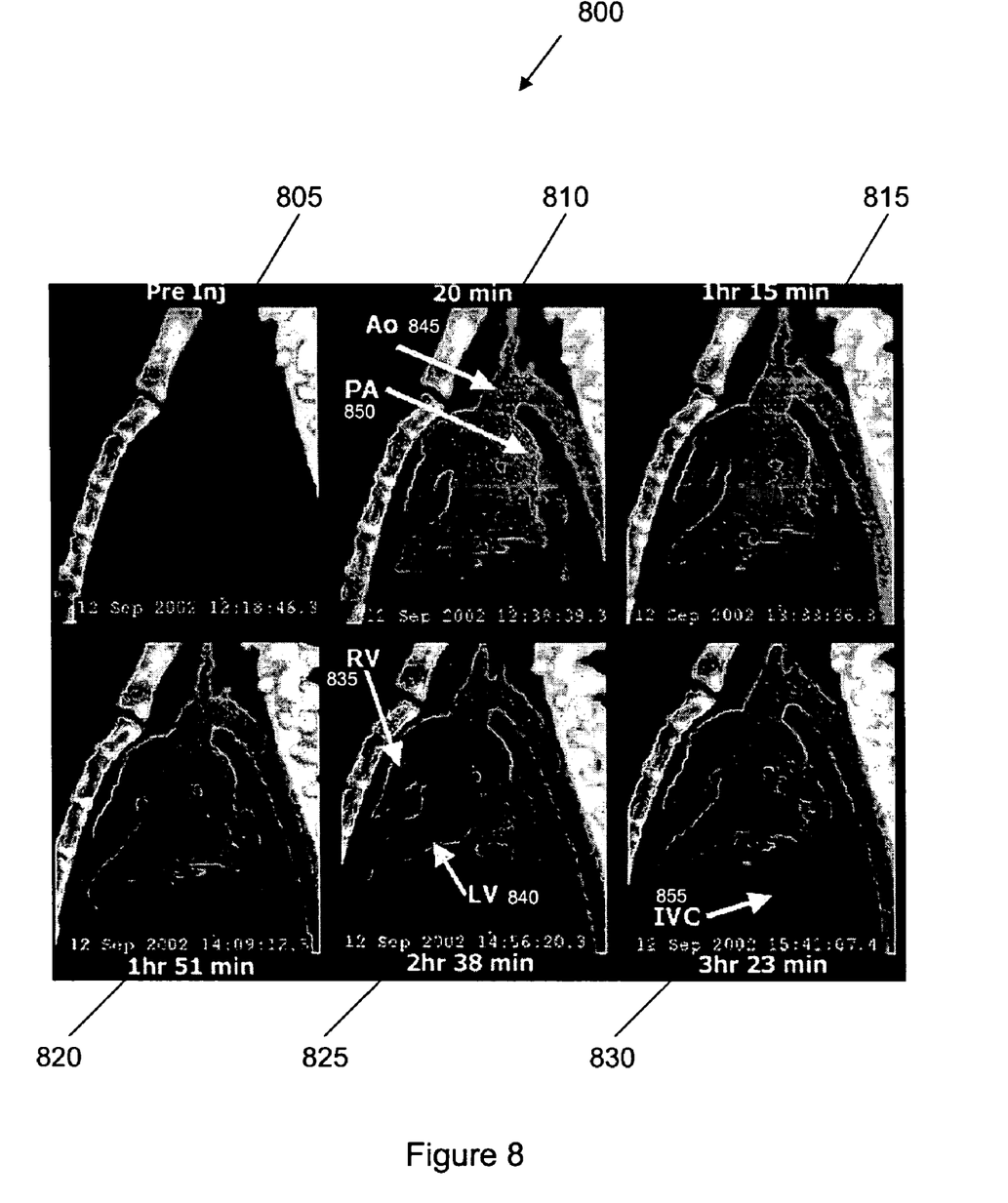
FIG. 8 shows example volume-rendered CT images of an in vivo rabbit heart 800 imaged before 805 and at multiple time sequences post injection 810, 815, 820, 825, 830 of one embodiment of liposomal iohexol. All volume-rendering parameters and display parameters were held constant across time points.

FIG. 8 shows volume images of the rabbit heart acquired pre-contrast 805 and at 20 minutes 810, 1 hour 15 minutes 815, 1 hour 51 minutes 820, 2 hour 38 minutes 825, and 3 hour 23 minutes 830 after administration of the liposomal iohexol formulation. All display and rendering parameters are identical for all images. The anatomies of all four heart chambers can be distinctly visualized along with the associated great vessels. Note that there may be absence of blood pool in the upper left panel 805 and the persistent enhanced opacity of the blood pool up to the final panel representing 3 hours 23 minutes post injection 830. Visible structures include: right ventricle 835 (RV); left ventricle 840 (LV); Aorta 845 (Ao); pulmonary artery 850 (PA); and the inferior vena cava 855 (IVC). These images demonstrated sustained contrast even 3 hours after administration of the liposomal iohexol.

FIG. 9 shows a thick-slab rendering of the heart obtained at ultrahigh resolution after the rabbit was euthanized and thus cardiac motion was eliminated. Labeled structures include the right ventricle 905 (RV); left ventricle 910 (LV); and aorta 915 (Ao).

FIG. 10 shows images of the left coronary artery of a rabbit under high magnification conditions at 3 hours after the second injection of the liposomal iohexol formulation. The left panel 1005 shows a 1.3 mm thick CT slice of in vivo rabbit heart imaged 3 hours 18 minutes after the second injection of one embodiment of liposomal iohexol. The right panel 1010 shows a volume rendered view of the same data set. The left coronary artery (shown as 1015 in 1010) was enhanced by 109 HU.

The above descriptions have referred to the preferred embodiments and selected alternate embodiments. Modifications and alterations will become apparent to persons skilled in the art upon reading and understanding the preceding detailed description. It is intended that the embodiments described herein be construed as including all such alterations and modifications insofar as they come within the scope of the appended claims or the equivalence thereof.

We claim:

1. A composition for enhancing contrast of one or more areas of a subject for X-ray imaging when administered to the subject, the composition comprising:
   liposomes, the liposomes encapsulating one or more iodinated nonradioactive contrast-enhancing agents, and the liposomes comprising: cholesterol, at least one phospholipid, and at least one phospholipid which is derivatized with a polymer chain,
   wherein the average diameter of the liposomes is less than 150 nanometers.

2. The composition of claim 1, wherein the X-ray imaging is computed tomography.

3. The composition of claim 1, wherein the iodinated nonradioactive contrast-enhancing agents are selected from at least one of: iodinated ionic compounds, iodinated nonionic compounds, and mixtures thereof.

4. The composition of claim 3, wherein a suspension of the liposomes has a concentration of at least 30 milligrams of iodine per milliliter of the suspension.

5. The composition of claim 1, wherein the average diameter of the liposomes is less than 120 nanometers.

6. The composition of claim 1, wherein the composition is capable of being administered to the bloodstream of the subject.

7. The composition of claim 6, wherein the composition provides an enhanced contrast that remains detectable at least 30 minutes after administration.

8. The composition of claim 6, wherein the composition provides an enhanced contrast of at least 50 Hounsfield units in at least part of at least one of a vasculature and an organ of the subject.

9. The composition of claim 1, wherein the liposomes are PEGylated liposomes.

10. The composition of claim 1, wherein the liposomes are targeted liposomes.

11. A composition for enhancing contrast of one or more areas of a subject for X-ray imaging when administered to the subject, the composition comprising liposomes, the liposomes comprising:
    at least one first lipid or phospholipid;
    at least one second lipid or phospholipid which is derivatized with one or more polymers; and
    at least one sterically bulky excipient capable of stabilizing the liposomes;
    wherein the average diameter of the liposomes is less than 150 nanometers, and wherein the liposomes encapsulate at least one iodinated nonradioactive contrast enhancing agent.

12. The composition of claim 11, wherein the at least one first lipid or phospholipid comprises 1,2-dipalmitoyl-sn-glycero-3-phosphocholine (DPPC).

13. The composition of claim 11, wherein the at least one second lipid or phospholipid which is derivatized with one or more polymers comprises N-carbamylmethoxypoly(ethylene glycol)-1,2-distearoyl-sn-glycerol-3-phosphoethanolamine (DSPL-MPLG2000).

14. The composition of claim 11, wherein the at least one sterically bulky excipient is selected from at least one of: sterols, fatty alcohols, fatty acids, and mixtures thereof.

15. The composition of claim 11, wherein the at least one sterically bulky excipient is cholesterol.

16. The composition of claim 11, wherein the liposomes are not autoclaved.

17. The composition of claim 11, wherein the liposomes are contained in a suspension medium, at least some of the iodinated nonradioactive contrast enhancing agent that has not been encapsulated by the liposomes having been removed from the suspension medium.

18. The composition of claim 11, wherein the at least one first lipid or phospholipid is present in the amount of about 55 to about 75 mol %; the at least one second lipid or phospholipid which is derivatized with one or more polymers is present in the amount of about 1 to about 20 mol %; and the at least one sterically bulky excipient is present in the amount of about 25 to about 40 mol %.

19. The composition of claim 18, wherein the at least one first lipid or phospholipid is hydrogenated soy phosphatidylcholine; the at least one second lipid or phospholipid which is derivatized with one or more polymers is N-carbamyl-methoxypoly(ethylene glycol)-1,2-distearoyl-sn-glycerol-3-phosphoethanolamine (DSPL-MPLG2000); and the at least one sterically bulky excipient is cholesterol.

* * * * *